United States Patent
Kata

(10) Patent No.: US 9,901,537 B1
(45) Date of Patent: Feb. 27, 2018

(54) HAIR COLOR STAIN PROTECTOR AND METHOD OF USE

(71) Applicant: Kamakshi Kata, Allen, TX (US)

(72) Inventor: Kamakshi Kata, Allen, TX (US)

( * ) Notice: Subject to any disclaimer, the term of this patent is extended or adjusted under 35 U.S.C. 154(b) by 0 days.

(21) Appl. No.: 15/725,141

(22) Filed: Oct. 4, 2017

Related U.S. Application Data

(60) Provisional application No. 62/403,779, filed on Oct. 4, 2016.

(51) Int. Cl.
  *A61K 8/9789* (2017.01)
  *A61K 8/9794* (2017.01)
  *A61Q 19/00* (2006.01)

(52) U.S. Cl.
  CPC .......... *A61K 8/9789* (2017.08); *A61K 8/9794* (2017.08); *A61Q 19/00* (2013.01); *A61K 2800/5922* (2013.01)

(58) Field of Classification Search
  CPC ..... A61K 8/9789; A61K 8/9794; A61Q 19/00
  See application file for complete search history.

(56) References Cited

U.S. PATENT DOCUMENTS

2008/0089916 A1* 4/2008 Magee .............. A61K 8/0229
                                                       424/401

* cited by examiner

*Primary Examiner* — Trevor Love
(74) *Attorney, Agent, or Firm* — Eldredge Law Firm; Richard G. Eldredge

(57) ABSTRACT

A hair color stain protector formula, having by volume about 9% *cocos nucifera* oil; about 1.25% candililla wax; about 40.8% Kahl VegoJelly 7036PLUS; about 40% floraesters; about 7% joboba oil; about 1.6% shaebutter; and about 0.35% lavender oil.

1 Claim, 1 Drawing Sheet

401

| | |
|---|---|
| Cocos Nucifera Oil | 9.0000 % |
| Candelilla Wax | 1.2500 % |
| Kahl Vego Jelly 7036PLUS | 40.8000 % |
| Floraesters | 40.0000 % |
| Jojoba Oil | 7.0000 % |
| Shea butter | 1.6000 % |
| Lavender Oil | 0.3500 % |
| | 100.0000 % |

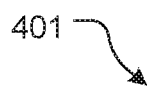
| | |
|---|---|
| Cocos Nucifera Oil | 9.0000 % |
| Candelilla Wax | 1.2500 % |
| Kahl Vego Jelly 7036PLUS | 40.8000 % |
| Floraesters | 40.0000 % |
| Jojoba Oil | 7.0000 % |
| Shea butter | 1.6000 % |
| Lavender Oil | 0.3500 % |
| | 100.0000 % |

HAIR COLOR STAIN PROTECTOR AND METHOD OF USE

BACKGROUND

1. Field of the Invention

The present invention relates generally to hair stains and colors, and more specifically, to a skin protector to protect a user's skin from becoming stained or colored during the hair coloring process.

2. Description of Related Art

Hair colors and stain systems are well known in the art and are effective means for a user to change their hair color. For example, users commonly purchase stain kits to use at home or go to a salon for this procedure to be done by a professional.

One of the problems commonly associated with conventional hair stains and colors is stain caused on the user's skin. Commonly, users apply various balms and lotions to protect their skin, however, these products can be toxic and damaging to skin. In addition, these products are rarely effective at adequately protecting the user's skin from the stain or color.

Accordingly, although great strides have been made in the area hair stains and colors, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 1 is a formula in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional hair colors and stains. Specifically, the present invention provides a hair color with gentle ingredients so as to not damage hair during the coloring process. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a formula for hair color stain protector on skin.

In the contemplated embodiment, the formula 401 includes 9 percent *cocos nucifera* oil; 1.25 percent candelilla wax; 40.8 percent Kahl VegoJelly 7036PLUS; 40 percent floraesters; 7 percent jojoba oil; 1.6 percent shea butter; and 0.35 percent lavender oil. It will be appreciated that the preferred embodiment could be modified in the percentages in alternative embodiments in addition to other types of materials added therewith. It should be appreciated that the exact items disclosed herein could vary based on brand and availability.

One of the unique features believed characteristic of the present application is the combination of the above ingredients in the same or similar percentages. It should be appreciated that this formula provides a novel skin protector, while being safe and non-toxic for use on the skin.

For reference, the current Kahl VegoJelly 7036PLUS may include one or more of Castor Seed Oil, Hydrogenated *Rhus Verniciflua* Peel Wax, *Rhus Succedanea* Fruit Wax, Ascorbyl Palmitate, and Tocopherol. Any other similar compound could easily be used in place of this ingredient. For additional reference, Floraesters are oil-free jojoba emollients that are commonly used in cosmetic products.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A hair color stain protector formula, comprising by volume:
   a) about 9% *cocos nucifera* oil;
   b) about 1.25% candelilla wax;
   c) about 40.8% of one or more of:
      castor seed oil;
      hydrogenated *rhus verniciflua* peel wax;
      *rhus succedanea* fruit wax;
      ascorbvl palmitate; and tocopherol;
   d) about 40% floraesters;
   e) about 7% jojoba oil;
   f) about 1.6% shea butter; and
   g) about 0.35% lavender oil.

* * * * *

UNITED STATES PATENT AND TRADEMARK OFFICE
CERTIFICATE OF CORRECTION

| | |
|---|---|
| PATENT NO. | : 9,901,537 B1 |
| APPLICATION NO. | : 15/725141 |
| DATED | : February 27, 2018 |
| INVENTOR(S) | : Kata et al. |

It is certified that error appears in the above-identified patent and that said Letters Patent is hereby corrected as shown below:

On the Title Page

Item (12) "Kata" is corrected to read --Kata et al.--.

Item (72) Inventor is corrected to read:
--Kamakshi Kata, Allen, TX (US);
Sreedhar Reddy Nalabolu, Hayward, CA (US)--.

Signed and Sealed this
Fourteenth Day of June, 2022

Katherine Kelly Vidal
*Director of the United States Patent and Trademark Office*